United States Patent [19]

Kramer

[11] 4,424,387

[45] Jan. 3, 1984

[54] ADAMANTYL CARBOXYLIC AND SULFONIC ACID CATALYZED PARAFFIN ISOMERIZATION

[75] Inventor: George M. Kramer, Berkeley Heights, N.J.

[73] Assignee: Exxon Research and Engineering Co., Florham Park, N.J.

[21] Appl. No.: 475,451

[22] Filed: Mar. 15, 1983

[51] Int. Cl.$^3$ .............................................. C07C 5/30
[52] U.S. Cl. ................................. 585/743; 585/740; 585/741; 585/745; 585/746; 585/747; 585/749
[58] Field of Search ............... 585/740, 741, 742, 743, 585/745, 746, 747, 749

[56] References Cited

U.S. PATENT DOCUMENTS

| | | | |
|---|---|---|---|
| 3,231,633 | 1/1966 | Kramer | 585/731 |
| 3,382,288 | 5/1968 | Schneider | 585/352 |
| 3,546,308 | 12/1970 | Moore | 585/352 |
| 3,671,598 | 6/1972 | Moore | 585/350 |
| 4,162,233 | 7/1979 | Kramer | 585/942 |
| 4,229,611 | 10/1980 | Kramer | 585/728 |
| 4,357,483 | 11/1982 | Kramer | 585/743 |
| 4,357,484 | 11/1982 | Kramer | 585/743 |

OTHER PUBLICATIONS

Albright et al., "Industrial Laboratory Alkylation", ACS Symposium Series 35, Washington, D.C., (1977), Chap. 1.
Mirada et al., J. Org. Chem., vol. 44, 2619–2624, (1979).
Van Pelt et al., J. Am. Chem. Soc., vol. 98, 5864–5870, (1976).

*Primary Examiner*—Delbert E. Gantz
*Assistant Examiner*—A. Pal
*Attorney, Agent, or Firm*—Robert J. North

[57] ABSTRACT

A process is described for paraffin isomerization under strong acid conditions in which an adamantyl carboxylic acid or sulfonic acid is used to substantially increase the reaction rate of the isomerization.

19 Claims, No Drawings

ADAMANTYL CARBOXYLIC AND SULFONIC ACID CATALYZED PARAFFIN ISOMERIZATION

BACKGROUND OF THE INVENTION

This invention relates to a catalytic process for paraffin isomerization producing branched paraffins under strong acid catalyzed conditions in the presence of adamantyl carboxylic or sulfonic acids, as hydride transfer catalysts.

Alkylation or isomerization of paraffins under strong acid conditions are well-known processes for producing a wide variety of useful hydrocarbon materials and particularly, gasoline additives. For example, 2,2,4-trimethylpentane is a common blending agent used for gasoline octane improvement which can be produced by alkylating isobutylene with isobutane in sulfuric acid or liquid HF. An example of such an acid-catalyzed reaction process is described in U.S. Pat. No. 3,231,633.

Hydrocarbon conversion processes employing novel Lewis acid systems are disclosed in U.S. Pat. No. 4,229,611 and U.S. Pat. No. 4,162,233, both assigned to Exxon Research and Engineering Company.

U.S. Pat. No. 3,671,598 describes a process for isomerizing saturated cyclic hydrocarbons under strong acid conditions in the presence of an adamantyl hydrocarbon. However, no suggestion is made that other specifically substituted adamantyl derivatives, particularly those with carboxy or sulfoxy substituents, might be more effective in increasing the rate of isomerization of paraffins to branched isomers.

U.S. Pat. Nos. 4,357,481; 4,357,484; 4,357,482; and 4,357,483 to George M. Kramer (issued Nov. 2, 1982, and assigned to Exxon Research and Engineering Company) disclose the use of adamantane hydrocarbons in paraffin-olefin alkylation and non-cyclic paraffin isomerization, and the use of aminoalkyladamantanes in paraffin-olefin alkylation and non-cyclic paraffin isomerization, respectively, in which rates of reaction are substantially increased as compared to the absence of the specifically disclosed adamantane. However, none of the patents disclose or suggest the use of carboxy- or sulfoxy-containing adamantanes as rate enhancing agents in alkylation or isomerization process.

New methods for producing such branched paraffinic hydrocarbons are constantly being searched for in an effort to improve isomerization efficiency. More active catalysts would enable these rearrangements to be conducted at lower temperatures where thermodynamic equilibria are more favorable to branched structures, an important factor in butane, pentane and hexane isomerization.

SUMMARY OF THE INVENTION

We have found that the presence of an adamantyl carboxylic or sulfonic acid in a strong acid system containing an isomerizable paraffinic hydrocarbon significantly increases the rate of isomerization of said hydrocarbon, presumably because the paraffin becomes involved in faster intermolecular hydride transfer reactions. Since inter-molecular hydride transfer is generally the rate-determining step in paraffin isomerization, (see "Industrial Laboratory Alkylation", edited by Lyle F. Albright and Arthur R. Goldsby, ACS Symposium Series 55, Published Washington, D.C., 1977, Chapter One, "Alkylation Studies" by G. M. Kramer) the presence of the adamantyl derivative acid will serve to significantly increase the reaction rate of the isomerization process. In the production of octane-increasing agents, this should lead to the utilization of smaller and more efficient reactors, which enhances the economics of the process.

More specifically, by this invention, there is provided an isomerization process comprising the step of contacting a $C_4$-$C_6$ paraffinic hydrocarbon with a strong acid system in the presence of an adamantyl carboxylic acid, adamantyl sulfonic acid, or mixture thereof, said adamantyl compound containing at least one unsubstituted bridgehead position, and said process being conducted at a temperature of about $-100°$ C. to $150°$ C., thereby producing a branched isomer of said paraffinic hydrocarbon.

DESCRIPTION OF THE INVENTION AND PREFERRED EMBODIMENTS

The reason that an adamantane carboxylic acid or adamantane sulfonic acid serves to increase the rate of intermolecular hydride transfer during branched paraffin isomerization, is not totally understood. One theory that we do not wish to be bound by is that reversible hydride transfer from the bridgehead position of the adamantyl group to a carbonium ion in solution is enhanced due to lack of steric repulsions in the transition state involving the adamantyl group, as compared to hydride transfer involving a paraffinic hydrocarbon and the same carbonium ion.

In the process, $C_4$-$C_6$ paraffinic hydrocarbons are isomerized. As is well-known, the extent of the rearrangement and the possibility of changing the degree of branching of the paraffin, as distinct from the possibility of inducing an alkyl shift, depends primarily on the acid system. The adamantane derivative catalyzes the process appropriate to the acid employed. Examples of operable paraffins include n-butane, isobutane, isopentane, n-pentane, 2-methylpentane, 3-methylpentane, n-hexane, mixtures thereof, and the like. Preferred paraffins in the process are 2- and 3-methylpentane, n-hexane, n-pentane and n-butane, or refinery streams containing mixtures of these components which are not at their equilibrium concentrations.

Both normal and branched paraffins can be used in the subject isomerization process, under very strong acid conditions, e.g., $AlBr_3$-$CH_2Br_2$ solutions. However, with slightly weaker acid systems, such as $H_2SO_4$ and HF, isomerizations are limited to the rearrangement of paraffins containing a tertiary carbon atom. Normal paraffins like n-butane do not generally undergo the isomerization process in these weaker acid systems.

The product paraffins in the process are $C_4$-$C_6$ branched paraffinic hydrocarbons. Representative examples include isobutane, isopentane, 2-methylpentane, 3-methylpentane, 2,3-dimethylbutane, 2,2-dimethylbutane, and the like. The preferred product paraffinic hydrocarbons in the process are the most highly branched isomers possibly derivable from each of the $C_4$, $C_5$ and $C_6$ product streams. The product paraffins are useful as gasoline blending agents for octane improvement and/or hydrocarbon solvents. Higher molecular weight paraffins may also be isomerized. However, it is generally known that such reactions are often accompanied by extensive side reactions. Specific requirements for the selective isomerization of such reagents are beyond the scope of this patent application.

The phrase "a strong acid system", as used herein, refers to the acid system capable of assisting in generating carbonium ions in the process and includes an "acid component" and a solvent, or one material that can function in both capacities, such as concentrated sulfuric acid, preferably being of initial acid strength of about 95 to 99 weight percent, or liquid HF. The acid system can be solid/liquid, liquid, or gaseous. Preferably the acid system is a liquid and particularly preferred is concentrated sulfuric acid as the acid system.

The strong acid components in the acid system are conventional protic, aprotic, or Lewis acids and include $AlBr_3$, $AlCl_3$, $GaCl_3$, $TaF_5$, $SbF_5$, $AsF_5$, $BF_3$, HF, HCl, HBr, $H_2SO_4$, $HSO_3F$, $CF_3SO_3H$, and the like and mixtures thereof. A preferred acid component in the process, when aimed at preparing most highly branched products, is $AlCl_3$, $AlBr_3$, $GaCl_3$, or $TaF_5$ used with a solvent as described hereinbelow. If a rapid but limited rearrangement is desired, $H_2SO_4$ or HF would be the preferred acids. An example of the former is the isomerization of n-hexane to dimethylbutanes and an example of the latter is the isomerization of 2-methylpentane to 3-methylpentane. Also, HCl and HBr are preferably not used alone, but are used in combination with other Lewis acids, e.g., $AlCl_3$ or $AlBr_3$.

Also a component of the "acid system", may be a solvent for the acid component as where the strong acid component is a solid material, e.g., $AlBr_3$. For Lewis acids, halogenated paraffins and aromatics can generally be used; representative examples include $CH_3Br$, $CH_2Br_2$, $CH_2Cl_2$, 1,2-dichloroethane, 1,2,3-trichlorobenzene, 1,2,3,4-tetrachlorobenzene, pentafluorobenzene, HF, $H_2SO_4$, $CF_3SO_3H$, $HSO_3F$ and the like, and mixtures thereof.

The molar concentration of acid component in the solvent, if they are different materials, is generally between 0.1 and 8.0 M, and preferably 0.5 to 4.0 M (moles/liter) based on solvent volume.

The volume ratio of the acid system to the paraffinic hydrocarbon to be isomerized is generally about 5:1 to 1:5, and preferably about 3:1 to 1:3 parts by volume. However, larger and smaller ratios can be effectively employed.

Isomerization reactions described herein are normally carried out in two-phase systems, i.e., an acid phase containing the adamantyl derivative acid and a hydrocarbon phase. The system can also be a partially miscible one where, for example, a paraffin, $AlBr_3$ and 1,2,3,4-tetrachlorobenzene are employed.

The adamantane acid compound useful in the process contains at least one carboxy or sulfoxy group, preferably being an alkylcarboxy or alkylsulfoxy group and at least one unsubstituted adamantyl bridgehead position, is preferably surface active, and can be prepared by conventional methods in the art. By the term "surface active", is meant that the adamantane acid compound depresses the surface tension of the acid system, and promotes formation of an emulsion between the acid phase and hydrocarbon phase, when used at low concentration, typically in the range of $10^{-6}$ to $10^{-1}$ moles/liter based on the liquid acid layer.

The adamantyl carboxylic acid or sulfonic acid is preferably of the formula:

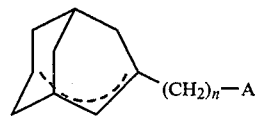

where n=0–16, preferably 1–12, most preferably 4–8, A=COOH or $SO_3H$, and wherein the adamantane ring and the alkyl chain can be further modified and substituted with groups which are inert under the process conditions and include $C_1$-$C_4$ alkyl groups, $NO_2$ and $CF_3$ or $C_nF_{2n+1}$ (where n=1–10) replacements for the remaining adamantyl bridgehead protons provided that at least one adamantyl bridgehead hydrogen remains to promote intermolecular hydride transfer.

Further included are adamantane compounds in which a total of 2 or 3 of the 4 bridgehead protons of the adamantane ring are replaced by a $(CH_2)_n$—COOH or $(CH_2)_n$—$SO_3H$ chain, n varying from 0 to 16.

The alkyl chains can also contain non-reactive branches, e.g., —$(CH_2)_n$—C—$(CH_3)_2$—$(CH_2)_m$—A, where n=(0–10), m=(0–10) and A is —$CO_2H$ or —$SO_3H$, where the total carbon chain is no more than 16 carbon atoms in length. The neopentyl structure existing in the above illustrated chain is non-reactive in all but the strongest acids and thus, can be used in concentrated $H_2SO_4$ or HF solutions. Expressly excluded is a single methyl group substitution, or its equivalent, which can form reactive tertiary carbonium ions in the process.

Representative examples include 16-(1'-adamantyl)-hexadecanoic acid, 12-(1'-adamantyl)dodecanoic acid, 4-(1'-adamantyl)butanoic acid, 3-(1'-adamantyl)-propanoic acid, 2-(1'-adamantyl)ethanoic acid, 1'-adamantyl carboxylic acid, 10-(1'-adamantyl) decanoic acid, 8-(1-adamantyl)octanoic acid, 6-(1'-adamantyl)-hexanoic acid, 6-(2'-adamantyl)hexanoic acid, 5-(1'-adamantyl)-2-methylpentanoic acid, 5-(1'-adamantyl)-pentanoic acid, 6-(1'-adamantyl)hexylsulfonic acid, 5-(1'-adamantyl)pentylsulfonic acid, 4-(1'-adamantyl)-butylsulfonic acid, 4-(2'-adamantyl)butylsulfonic acid, 12-(1'-adamantyl)dodecanoic acid, and the like. A preferred catalyst compound is 6-(1'-adamantyl)hexanoic acid. It should also be noted that readily solvolyzed derivatives of these acids and their equivalents such as their esters, anhydrides, acylhalides and amides, which generate the corresponding free acid through solvolysis under "protic acid" reaction conditions, can generally be used in place of the parent adamantane compounds and are included within the scope of the claimed subject process.

The molar concentration of adamantyl compound in the acid solution varies from about $10^{-6}$ to $10^{-1}$ moles/liter, and preferably about $10^{-4}$ to $10^{-2}$ moles/liter. However, larger and smaller ratios can also be used effectively.

Temperatures in the process are conducted in the range of about $-100°$ to 150° C. and preferably about $-50°$ to 100° C., depending primarily on the temperature required to obtain a liquid-phase catalyst.

The process is normally carried out at atmospheric pressure but may also be conducted at higher pressures up to about 20 atmospheres, the pressure depending primarily on the partial pressure of isobutane in the reaction mixture.

Yields of isomeric hydrocarbons in the process are only limited by the thermodynamic equilibrium at the process temperature, and it is within the scope of this invention to separate product isomers and recycle the starting material and less desirable product materials for further conversion to the more desirable isomers.

A particularly preferred embodiment of the process is where n-butane is isomerized to isobutane, n-pentane is isomerized to isopentane, and n-hexane is isomerized to a mixture of methylpentanes and dimethylbutanes.

Apparatus for carrying out the subject process is conventional, either in a laboratory, pilot plant, or full industrial scale, and the process can be conducted in a batch-type operation or in a continuous-type operation in liquid/liquid or liquid/gas systems. The adamantyl compound may also be used in solid/liquid or solid/gas systems, wherein its polar functionality is adsorbed onto or bound by a highly acidic solid acid. A preferred process is a liquid/liquid system conducted in a continuous manner.

Generally, the process is conducted by contacting a liquid mixture of paraffin with the adamantyl compound in the acid system described herein. If the acid system is, for example, concentrated $H_2SO_4$, the process is conducted in an emulsion of the two-phase system, the acid phase usually being the continuous phase, although this is not essential to the process. The entire system is preferably at reaction temperature at time of mixing, during which the entire system is vigorously mixed, stirred and agitated to insure good contact between the acid and hydrocarbon phases. The reaction is allowed to progress until a desired or substantial quantity of formed product is obtained. This can be monitored by analytical methods such as gas chromatography and mass spectrometry. After the desired paraffinic product has been formed, the phases can be separated and the hydrocarbon phase treated by extraction or fractional distillation, and the like, to separate out and collect the desired product.

It is to be understood that obvious modifications and variations on the above-described procedure and subject process, not specifically described herein, are deemed to be encompassed within the general scope and spirit of this application.

The following example is illustrative of the best mode of carrying out the invention, as contemplated by me, and should not be construed as being limitations on the scope or spirit of the instant invention.

EXAMPLE 1

This example illustrates the effect of surface active adamantyl carboxylic acids in accelerating intermolecular hydride transfer at a sulfuric acid/hydrocarbon interface resulting in faster isomerization of a branched paraffin, i.e., 3-methylpentane to 2-methylpentane. Listed in the Table are the relative isomerization rates of 3-methylpentane, obtained under well-stirred two-phase conditions, using equal volumes of the 3-methylpentane and 96% sulfuric acid, which contained the listed adamantyl carboxylic acids. For comparison, the isomerization rate with no adamantyl additive is also listed.

The no additive run was conducted by mixing 100 ml. of conc. $H_2SO_4$, (96%) with 100 ml. of 3-methyl-pentane in a 500 ml., 2-neck flask at room temperature and atmospheric pressure. The two-phase system was stirred vigorously and samples of the upper hydrocarbon phase were withdrawn periodically and analyzed by gas chromatography for the extent of isomerization. The reaction was then individually repeated with 0.002 M. solutions of the three listed adamantylalkyl carboxylic acids in sulfuric acid. The relative isomerization rates in the systems were measured. As seen in the data, the net isomerization rate of 3-methylpentane to 2-methylpentane more than tripled when a 0.002 M. solution of any one of the adamantylalkyl carboxylic acids used, as compared to the no additive control. Also seen is the fact that increasing the carbon chain length of the alkanoic acid had a significant effect on increasing the isomerization rate.

TABLE

Comparison of Surface Active Hydride Transfer Catalysts in $H_2SO_4$

| Catalyst[a] | 3 Methylpentane Isomerization, Rel. Rate[b] |
|---|---|
| None | 1 |
| 1'-Ad-$(CH_2)_3$COOH | 3.5 |
| 1'-Ad-$(CH_2)_4$COOH | 3.9 |
| 1'-Ad-$(CH_2)_5$COOH | 7.1 |

[a]Adamantyl catalysts used in 0.002 M. concentrations, in concentrated $H_2SO_4$, 96%, at 23 ± 1° C.
[b]Relative isomerization rates based on the control run in the absence of adamantyl catalyst.

What is claimed is:

1. An isomerization process comprising the step of contacting a $C_4$–$C_6$ paraffinic hydrocarbon with a strong acid system in the presence of an adamantyl carboxylic acid, adamantyl sulfonic acid, or mixture thereof, said adamantyl containing at least one unsubstituted bridgehead position, and said process being conducted at a temperature of about $-100°$ C. to $150°$ C., thereby producing a branched isomer of said paraffinic hydrocarbon.

2. The process of claim 1 wherein said paraffinic hydrocarbon is selected from 3-methylpentane, 2-methylpentane, n-hexane, n-pentane, n-butane, isomers thereof, and mixtures thereof.

3. The process of claim 1 wherein said acid system contains an acid component selected from $AlCl_3$, $AlBr_3$, $GaCl_3$, $TaF_5$, $SbF_5$, $AsF_5$, $BF_3$, HF, HBr, HCl, concentrated $H_2SO_4$, $HSO_3F$, $CF_3SO_3H$, and mixtures thereof.

4. The process of claim 3 wherein said acid system further contains a solvent selected from $CH_3Br$, $CH_2Br_2$, $CH_2Cl_2$, 1,2-dichloroethane, 1,2,3-trichlorobenzene, 1,2,3,4-tetrachlorobenzene, HF, concentrated $H_2SO_4$, $HSO_3F$, $CF_3SO_3H$, and mixtures thereof.

5. The process of claim 3 wherein said acid component is concentrated $H_2SO_4$.

6. The process of claim 1 wherein said adamantyl carboxylic acid or adamantyl sulfonic acid is of the formula:

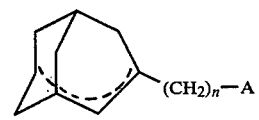

where n=0–16, A=COOH or $SO_3H$, and wherein the adamantyl ring and alkylene chain can be substituted with substituents which are inert or unreactive under the process conditions.

7. The process of claim 6 wherein A in said formula is COOH.

8. The process of claim 7 wherein said adamantane carboxylic acid is 4-(1'adamantyl)butanoic acid, 5-(1'-adamantyl)pentanoic acid, or 6-(1'-adamantyl)hexanoic acid.

9. The process of claim 8 wherein said adamantylalkyl carboxylic acid is 6-(1'-adamantyl)hexanoic acid.

10. The process of claim 1 wherein said adamantyl acid is present in a concentration of about $10^{-6}$ to $10^{-6}$ moles per liter based on said strong acid system.

11. The process of claim 1 wherein said temperature is in the range of about $-50°$ to $100°$ C.

12. The process of claim 1 being conducted in a continuous manner.

13. The process of claim 1 wherein said branched paraffin is 3-methylpentane, said product is 2-methylpentane and said acid system is $H_2SO_4$.

14. The process of claim 1 wherein said strong acid system contains $AlCl_3$, $AlBr_3$, $GaCl_3$, or $TaF_5$.

15. The process of claim 14 wherein n-butane is isomerized to isobutane.

16. The process of claim 14 wherein n-pentane is isomerized to isopentane.

17. The process of claim 13 wherein n-hexane is isomerized to a mixture of dimethylbutanes and methylpentanes.

18. The process of claim 14 wherein said paraffin is a mixture of $C_4$, $C_5$ or $C_6$ isomers, wherein at least one carbon fraction is not at thermodynamic equilibrium.

19. An isomerization process comprising the step of contacting 3-methylpentane with concentrated sulfuric acid containing 6-(1'-adamantyl)hexanoic acid, present in about 0.002 molar concentration, at ambient temperature and pressure thereby producing 2-methylpentane.

* * * * *